(12) United States Patent
Schrul et al.

(10) Patent No.: US 10,561,799 B2
(45) Date of Patent: Feb. 18, 2020

(54) DRIVE UNIT AND INJECTION DEVICE

(71) Applicant: TecPharma Licensing AG, Burgdorf (CH)

(72) Inventors: Christian Schrul, Burgdorf (CH); Markus Tschirren, Burgdorf (CH); Susanne Schenker, Langenthal (CH); Patrick Hostettler, Hasle (CH); Ursina Streit, Schonbuhl (CH)

(73) Assignee: TecPharma Licensing AG, Burgdorf (CH)

( * ) Notice: Subject to any disclaimer, the term of this patent is extended or adjusted under 35 U.S.C. 154(b) by 206 days.

(21) Appl. No.: 15/850,239

(22) Filed: Dec. 21, 2017

(65) Prior Publication Data

US 2018/0110926 A1    Apr. 26, 2018

Related U.S. Application Data

(63) Continuation of application No. PCT/CH2016/000093, filed on Jun. 16, 2016.

(30) Foreign Application Priority Data

Jun. 23, 2015 (CH) .......................... 904/15
Apr. 21, 2016 (CH) .......................... 531/16

(51) Int. Cl.
*A61M 5/31* (2006.01)
*A61M 5/315* (2006.01)
(Continued)

(52) U.S. Cl.
CPC ...... *A61M 5/31581* (2013.01); *A61M 5/1454* (2013.01); *A61M 5/2033* (2013.01);
(Continued)

(58) Field of Classification Search
CPC .... A61M 2005/2013; A61M 2005/202; A61M 2005/2086; A61M 2005/3143;
(Continued)

(56) References Cited

U.S. PATENT DOCUMENTS

2014/0350481 A1  11/2014  Raab et al.
2018/0169346 A1   6/2018  Hostettler et al.

FOREIGN PATENT DOCUMENTS

EP    2692377 A1   2/2014
EP    2881131 A1   6/2015
(Continued)

OTHER PUBLICATIONS

"International Preliminary Report on Patentability for Application No. PCT/CH2016/000084", dated Dec. 26, 2017, 8.
(Continued)

*Primary Examiner* — Imani N Hayman
(74) *Attorney, Agent, or Firm* — Dorsey & Whitney LLP

(57) ABSTRACT

A spring assembly for an administering device includes a driving spring configured as a spiral spring and a spring shaft. An inner end of the spring is rotationally fixedly attached to the spring shaft. A spring sleeve extends around the circumferential region of the spring, wherein the outer end of the spring is connected to the spring sleeve in a rotationally fixed manner and a disk-type spring-sleeve cover is attached to the spring sleeve or the spring shaft. The flange and the spring-sleeve cover extend radially away from an axis of the spring shaft and the flange is arranged near a distal end of the spring shaft. A radial stop is arranged on the flange periphery, and a blocking element is arranged on the spring sleeve to be complementary to the radial stop for releasably rotationally securing to each other when the blocking element and the radial stop engage.

19 Claims, 12 Drawing Sheets

(51) Int. Cl.
*A61M 5/20* (2006.01)
*A61M 5/32* (2006.01)
*A61M 5/145* (2006.01)

(52) U.S. Cl.
CPC ...... *A61M 5/3157* (2013.01); *A61M 5/31585* (2013.01); *A61M 5/31586* (2013.01); *A61M 5/3204* (2013.01); *A61M 2005/202* (2013.01); *A61M 2005/2013* (2013.01); *A61M 2005/2086* (2013.01); *A61M 2205/581* (2013.01); *A61M 2205/582* (2013.01); *A61M 2207/00* (2013.01)

(58) Field of Classification Search
CPC .. A61M 2005/3152; A61M 2005/3247; A61M 2005/3267; A61M 2205/3341; A61M 2205/581; A61M 2205/582; A61M 2207/00; A61M 5/1454; A61M 5/20; A61M 5/2033; A61M 5/3157; A61M 5/31581; A61M 5/31583; A61M 5/31585; A61M 5/31586; A61M 5/3159; A61M 5/3204; A61M 5/326; A61M 5/46; A61M 5/484
See application file for complete search history.

(56) References Cited

FOREIGN PATENT DOCUMENTS

| | | |
|---|---|---|
| WO | 2007115424 A1 | 10/2007 |
| WO | 2014111370 A1 | 7/2014 |
| WO | 2014154491 A1 | 10/2014 |
| WO | 2014166887 A1 | 10/2014 |
| WO | 2014166914 A1 | 10/2014 |
| WO | 2014170267 A1 | 10/2014 |
| WO | 2014191189 A1 | 12/2014 |
| WO | 2015032455 A1 | 3/2015 |
| WO | 2015055642 A1 | 4/2015 |
| WO | 2016007800 A1 | 1/2016 |
| WO | 2016071483 A1 | 5/2016 |

OTHER PUBLICATIONS

"International Preliminary Report on Patentability for Application No. PCT/CH2016/000093", dated Dec. 26, 2017, 7.

"International Search Report for Application No. PCT/CH2016/000084", dated Jul. 12, 2016, 3.

"International Search Report for Application No. PCT/CH2016/000093", dated Aug. 5, 2016, 3.

DRIVE UNIT AND INJECTION DEVICE

CROSS-REFERENCE TO RELATED APPLICATIONS

This application is a continuation of International Application No. PCT/CH2016/000093 filed Jun. 16, 2016, which claims priority to Swiss Application No. 00531/16 filed Apr. 21, 2016 and Swiss Application No. 00904/15 filed Jun. 23, 2015.

BACKGROUND

The invention relates to a spring assembly for an injection device, to a corresponding injection device and to a method for assembling these injection devices. In particular, the invention relates to an improved drive unit for an injection device and to a method for assembling this drive unit in the injection device.

Here, the term "drug" comprises any flowable medical formulation which is suitable for controlled administration through a means such as, for example, a cannula or hollow needle, comprising, for example, a liquid, a solution, a gel or a fine suspension containing one or more medical active substances. Drug can refer to a composition with a single active substance or to a premixed or co-formulated composition with a plurality of active substances from a single container. Drug or product comprises medicines such as peptides (for example, insulins, insulin-containing drugs, GLP-1-containing preparations as well as derived or analogous preparations), proteins and hormones, biologically prepared or active substances, active substances based on hormones or genes, nutrition formulations, enzymes and other substances either in solid (suspended) or liquid form but also polysaccharides, vaccines, DNA or RNA, or oligonucleotides, antibodies or parts of antibodies as well as suitable base substances, adjuvants and carrier substances.

WO2014/170267 discloses injection devices with a compact energy storage. The energy storage comprises at least two mutually connected spiral springs which can have sufficient energy stored, i.e., which are pretensioned, in order to empty an entire drug container. The document discloses no details on how the spiral springs can be pretensioned.

WO2014/154491 discloses an energy storage unit for an administration device. This energy storage unit comprises a pretensioned pressure spring, wherein the unit has a transport locking mechanism which is intended to prevent accidental activation of the energy storage unit. For the administration of viscous drugs, compressive springs have to have large and long dimensions, so that the administration devices also have to have larger dimensions. Then, in order to be able to achieve a regular administration of a drug, pressure springs have to be pretensioned sufficiently, which, in the case of the use of finished syringes made of glass as a drug container, increases the risk of glass breakage due to triggering of the administration device.

Therefore, it would be desirable to have energy storage units available that can be transported easily with stored energy and that can also be fitted geometrically into known administration devices.

SUMMARY OF THE INVENTION

Therefore, an aim of the invention is to indicate an improved energy storage for an administration device which enables the dispensing of highly viscous drugs and in the process can be produced cost effectively while also allowing a cost-effective production of the administration device.

The aim is achieved with a spring assembly, an administration device as well as a method for assembling a spring assembly according to the independent claims. Advantageous aspects can also be obtained from the dependent claims, the description and the figures.

An aspect of the invention relates to a spring assembly for an administration device, comprising a spring which is designed as a driving spring or a spiral spring, and a spring shaft with a firmly attached flange, wherein the inner end of the spring is at least attached to the shaft in a rotationally fixed manner. Furthermore, the spring assembly comprises a spring sleeve which extends at least partially around the lateral or circumferential area of the spring, wherein the outer end of the spring is connected to the spring sleeve in a rotationally fixed manner, and a disk-like spring sleeve cover which can be axially fixedly attached to the spring sleeve or to the spring shaft, wherein the disk diameter of the spring sleeve cover is less than or equal to that of the spring sleeve. The spring shaft defines an axis, has a proximal end and a distal end, wherein flange and spring sleeve cover extend radially away from the axis, and the flange is arranged near the distal end of the spring shaft. Wherein, furthermore, at least one radial stop is arranged on the periphery of the flange, and at least one blocking device or blocking means is arranged on the spring sleeve so as to be complementary to the at least one radial stop, such that the spring sleeve and the spring shaft are releasably rotationally secured in relation to each other when the blocking means and the radial stop engage.

In another aspect, the invention relates to a spring assembly, in which the axial positioning of the spring is defined by the fixed position of the flange and a variable axial fixation of the spring sleeve cover is defined, and thereby springs with different axial extension can be used in the spring assembly.

Wherein, in a further aspect, the spring sleeve cover can be shifted into the spring sleeve, wherein, on its periphery, the spring sleeve cover comprises at least one snap element, and the spring sleeve, complementarily thereto, comprises at least one recess for the at least one snap element, in order to fasten the spring sleeve cover to the spring sleeve.

Wherein, in another aspect, the spring sleeve comprises at least one recess in several axial positions for the at least one snap element of the spring sleeve cover, so that the spring sleeve cover can be fastened in different axial positions to the spring sleeve.

In an aspect, the spring can consist of a spirally wound band material, preferably made of a metal band material, particularly preferably band-shaped steel.

In another aspect, the invention comprises a spring assembly as described, wherein the spring sleeve is arranged coaxially to the spring shaft, characterized in that, on the spring sleeve, at least one flexible arm is arranged, which extends in a circumferential direction of the spring sleeve, which is attached firmly by one end to the spring sleeve and at the other end it can be deflected in the radial direction, and wherein, at the free end, the blocking means is arranged, in particular in the form of a tooth, which, due to deflection of the at least one flexible arm of the flexible arm can be made to engage with the radial stop or can be released from the engagement, so that the flexible arm together with the blocking means can form a locking snap device. Moreover, at the free end of the arm, a control arm can be arranged with axial offset in a distal direction toward the blocking means, and wherein, in case of radial deflection of the control arm, the blocking means can also be radially moved correspondingly and vice versa.

In another aspect, the spring shaft can comprise an axially formed holding rib, in which the inner end of the spring, which is formed as a holding flap, can be anchored in a rotationally fixed manner, and wherein the spring sleeve comprises an axially oriented holding structure, on which the outer end of the spring, which is formed as holding flap, can be anchored in a rotationally fixed manner.

According to a design, the spring can be pretensioned by a relative rotation of the spring sleeve toward the spring shaft, and wherein this pretensioning can be held by an engagement of radial stop and blocking means, and wherein the pretensioning can correspond to a torque of 1 to 100 newton/millimetre (N/mm), preferably a torque of 30 to 80 N/mm, and particularly preferably a torque from 60 to 70 N/mm.

In an aspect, the invention relates to an administration device for administering a liquid product, the administration device having a longitudinal axis and a housing with a mechanism holder which is connected firmly to the housing. Moreover, the administration device comprises a release device as well as a product container, in particular in the form of a prefilled syringe or carpula, which is arranged at least axially fixedly to a part of the housing, wherein, in the product container, an axially shiftable stopper is arranged, by means of the shifting of which in the distal direction a product can be dispensed from the product container. Furthermore, the administration device comprises a spring assembly according to the invention, in which energy for the automatic dispensing of product is stored, wherein the spring assembly is operatively connected to the release device, and wherein the spring sleeve is connected to the housing in a rotationally fixed manner, a threaded rod arranged coaxially relative to the longitudinal axis, which is connected to the spring shaft in a rotationally fixed manner, a piston rod arranged coaxially relative to the longitudinal axis, which is guided axially shiftably and in a rotationally fixed manner in the mechanism holder, wherein the piston rod can interact with the stopper of the product container in such a manner that, in the case of axial movement of the piston rod in the distal direction, the stopper can also be shifted in the distal direction, wherein the structure of the piston rod is sleeve-like and, via threaded elements on an inner surface of the piston rod, it is in threaded engagement with the threaded rod, so that a rotation of the threaded rod results in an axial shifting of the piston rod.

The invention moreover relates to a method for assembling a spring assembly with a pretensioned driving spring configured as a spiral spring in an administration device for administering a liquid product, in particular an elongate injection device, with a housing and a mechanism holder rigidly connected to the housing comprising at least the following steps:
a) the spring assembly is shifted axially onto a preassembled drive unit of the administration device which comprises the mechanism holder, as a result of which a rotatable driving member present in the drive unit is connected to a spring shaft of the spring assembly in a rotationally fixed manner, and whereby a release element arranged firmly on the mechanism holder is shifted in front of a control arm of the spring assembly.
b) a housing part or closure part of the administration device is shifted in the distal direction axially over the spring assembly, whereby the outer lateral surface of the spring assembly is connected in a rotationally fixed manner to the housing part or closure part.
c) the housing part or closure part is turned relative to spring assembly and preassembled drive unit, whereby the guide elements of the mechanism holder are guided in guides of the housing part or closure part, wherein the guide extends along the periphery of the housing part or closure part, wherein due to the turning, the release element moves the control arm radially outward and thus releases a torque present in the spring assembly, whereby an additional relative rotation between housing part or closure part and the mechanism holder is triggered until a radial block of the spring assembly engages with a radial stop of the mechanism holder and in this manner frictional locking connection between spring assembly and mechanism holder is produced.

In an aspect of the invention, the invention relates to an administration device which was assembled according to the method described in the previous paragraph, wherein the driving or spiral spring is wound in such a manner that the torque which acts on the outer lateral surface of the spring assembly after the release of the torque, points, compared to the part of the guide extending along the periphery on the housing part, in the opposite tangential direction.

In an aspect, the invention relates to an administration device, which was assembled according to the method described in the preceding paragraph, wherein the administration device is an autoinjector or an injection pen with automatic administration.

In an aspect, the invention relates to an administration device, which was assembled according to the method described in the preceding paragraph, wherein the administration device is a "patch" apparatus.

The term "distal" relates to the geometric end of the administration device at which the drug comes out during administration. The term proximal thus relates to the opposite end. In a pen-like injection apparatus device, the distal end corresponds to the end with the injection needle tip.

The term "radial stop" relates to a stop which can prevent relative rotation between two parts. A radial stop consists, for example, of a flat structure whose surface normal is tangential to a virtual circle generated by rotation.

In an aspect of the invention, a spring assembly for an administration device is disclosed, which consists of at least one spring shaft, a spring, in particular a spiral or clock spring, and a spring sleeve. The spring can be mechanically tensioned, and subsequently exert a torque on the spring shaft or the spring sleeve. The spring is connected by one end to the shaft and by the other end to the sleeve.

In an advantageous arrangement, the spring is a spiral spring, which is wound around the spring shaft and whose inner end is connected to the spring shaft. In this arrangement, the outer end of the spring is connected to the spring sleeve, wherein the spring sleeve forms a jacket for the spring. In this arrangement, the spring can be tensioned in that the spring sleeve is turned relative to the spring shaft.

In an advantageous arrangement, the spring sleeve can be secured against turning relative to the spring shaft. Here, on the spring sleeve, a blocking element can be firmly arranged, and, on the spring shaft, an element formed complementary thereto can be firmly arranged—elements which during interaction can function as anti-rotation device. By moving one of the elements, the anti-rotation device can then be released. The blocking element can be formed in particular as a locking snap device which can engage in a radial stop on the spring shaft. Here, the locking snap device can be arranged as a flexible arm on the spring sleeve or be part of the sleeve. On a free end of the arm, for example, a tooth can then be arranged, which can be made to engage with the radial stop. The engagement between stop and tooth can be released outwardly by a movement of the free end of the arm, in particular a movement in the radial direction.

In an advantageous combination, the spring assembly can comprise a pretensioned spring, wherein the spring tension can be held by the above-described anti-rotation device. In an advantageous addition, the spring assembly comprises a cover element and a bottom element. In another aspect, the bottom element is arranged as a flange firmly on the spring shaft, and the cover element is formed as a separate element, which can be fixed at variable separation from the bottom element on the spring shaft and/or on the spring sleeve, so that the spring can be protected from external mechanical influences. Subsequently, the spring assembly can be transported with a pretensioned spring. The spring can be supported and/or guided by the bottom element and/or cover element. In an alternative design, the spring assembly can also contain two, three or more pretensioned springs, preferably with a cover element for each spring.

In an advantageous arrangement, the spring consists of a spiral-shaped band material, wherein the spring parameters such as the spring constant are determined by the width of the band inter alia. The above-described arrangements advantageously make it possible to install different stiff springs with identical spring shaft (also with flange), identical spring sleeve and identical cover element. The band material used can be a metal, in particular steel, or a plastic.

In another aspect of the invention, an administration device is disclosed, in which a spring assembly according to one of the above arrangements can be installed, wherein the spring assembly can be used as a drive means. The type of administration device can be a pen-like injection device with a drug storage, in particular an autoinjector or an autopen. Here, the pen-like injection device can be designed for the administration of precisely one dose or of several doses. The injection device can also comprise a means by means of which the size of the dose can be selected in a targeted manner. The spring assembly is pretensioned in advantageous forms, so that the drug storage can be administered partially or completely by the energy stored in the spring. In another interesting design, more energy is stored in the spring assembly than is needed for administering a drug storage. As a result, the spring assembly can also be used, in particular, in reusable injection devices. Alternatively, the spring assembly can also be designed so that the spring can be tensioned by a user, for example, when replacing the drug storage or when setting a dose.

In an alternative aspect, an administration device is disclosed, in which a spring assembly according to one of the above arrangements can be installed, wherein here too the spring assembly can be used as a drive means. In this alternative aspect, the type of administration device can be an injection or infusion device which, in particular, can be applied directly to the skin of a patient by a bonding connection. Such devices are known to the person skilled in the art as "patch injector" or "patch pump." In another design of the aspect, the spring assembly can be used not only as drive means for the administration process, but also alternatively as a drive means for sticking in the administration cannula through which a product is administered.

In another aspect of the invention, a method is disclosed for assembling a spring assembly in an administration device. Here, the administration device can be a pen-like injection device. Alternatively, the device can also be the above-mentioned "patch" apparatuses.

In an advantageous design of the method for assembling the spring assembly into the administration device, the administration device is a pen-like injection device, in particular an autoinjector or an autopen. In the assembling of the spring assembly, the spring assembly is arranged on a preassembled drive unit, as described below. The preassembled drive unit here consists of at least one spring recess, in particular a mechanism holder, and a driving member arranged movably, in particular rotatably, in the spring recess or mechanism holder. In an embodiment with a mechanism holder, the driving member can be a threaded rod, which has a longitudinal guide on its proximal end.

In this embodiment, in a first assembly step, the spring assembly is shifted onto the proximal end of the preassembled drive unit. Here, the described threaded rod is brought into a rotationally fixed connection with the spring shaft, so that a rotational movement of the shaft is transmitted to the threaded rod. In the spring assembly, in this state, blocking means of the spring sleeve and the element complementary thereto are engaged, so that the spring of the spring assembly can be pretensioned. Furthermore, on the mechanism holder, a release element is arranged which, during the shifting of the spring assembly relative to the blocking means reaches a releasing position. From this releasing position, an additional relative movement between release element and blocking means is possible, by means of which the engagement between blocking means and the complementary element is released. In this so-called trigger position, a relative turning between spring shaft and spring sleeve is possible, which means that, in this state, torque can be guided from the spring toward the outside of the spring assembly.

In a second assembly step, a housing part of the injection device is shifted in the distal direction over the spring assembly and also at least partially over the preassembled drive unit. In the process, the spring sleeve is rotationally secured with respect to the housing part. Furthermore, a connection between mechanism holder and a housing part is established, which consequently then connects housing and mechanism holder of the injection device firmly to one another.

In an advantageous design of the connection between mechanism holder and housing part, the connection is established by a bayonet closure. This type of connection has the advantage that, in the establishment of the firm connection, the release element of the mechanism holder can also be moved from the releasing position into the released position. For this purpose, on the periphery of the mechanism holder, bayonet lugs can be arranged, which can engage with bayonet slots on an inner surface of the housing part. The bayonet slots here have at least one part extending axially and at least another portion extending in the circumferential direction. In the second assembly step, the bayonet slots engage with the axially extending part of the bayonet slots, so that the housing part can be shifted over the mechanism holder. At the end of this movement, the spring sleeve is connected in a rotationally fixed manner to the housing.

In the following third assembly step, the mechanism holder is turned relative to the housing part, wherein the movement is guided by the portion of the bayonet slot, which extends in the circumferential direction and wherein the bayonet is closed. At the same time, since the spring sleeve is now rotationally fixed relative to the housing part, a relative movement between mechanism holder and spring sleeve occurs, which results in the release element being moved from the releasing position into the released position.

In an alternative design, the spring recess can also be connected via a snap connection to a housing part formed as closure part. Wherein the snap connection replaces the first part of the bayonet closure, and the closure part, after the snap connection, is mounted rotatably in the spring recess, so that the above third assembly step can be carried out in the same way as with the bayonet closure.

Alternatively, the connection between spring recess and closure part can also be formed by threaded parts.

BRIEF DESCRIPTION OF THE DRAWINGS

FIGS. 5a-5b are a view of a spring assembly according to the invention from a distal position, wherein FIG. 5b reproduces a detail B from FIG. 5a.

DETAILED DESCRIPTION

FIGS. 1-10d show a spring assembly according to the invention with a corresponding injection device, an autoinjector, as well as the different assembly steps of the associated method according to the invention.

Figure 11:
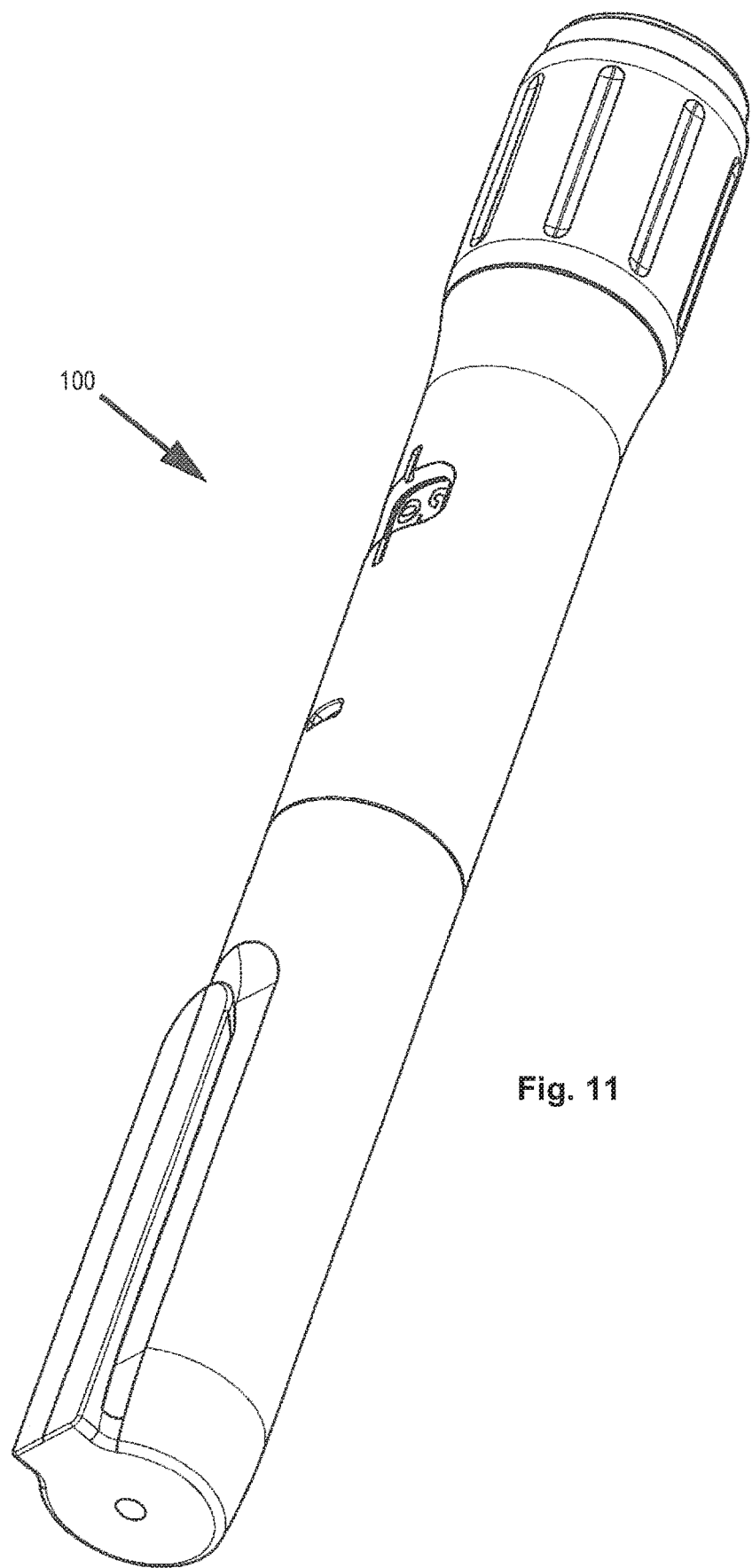
FIG. 11 is an external view of an alternative injection device according to the invention.
Figure 12A:
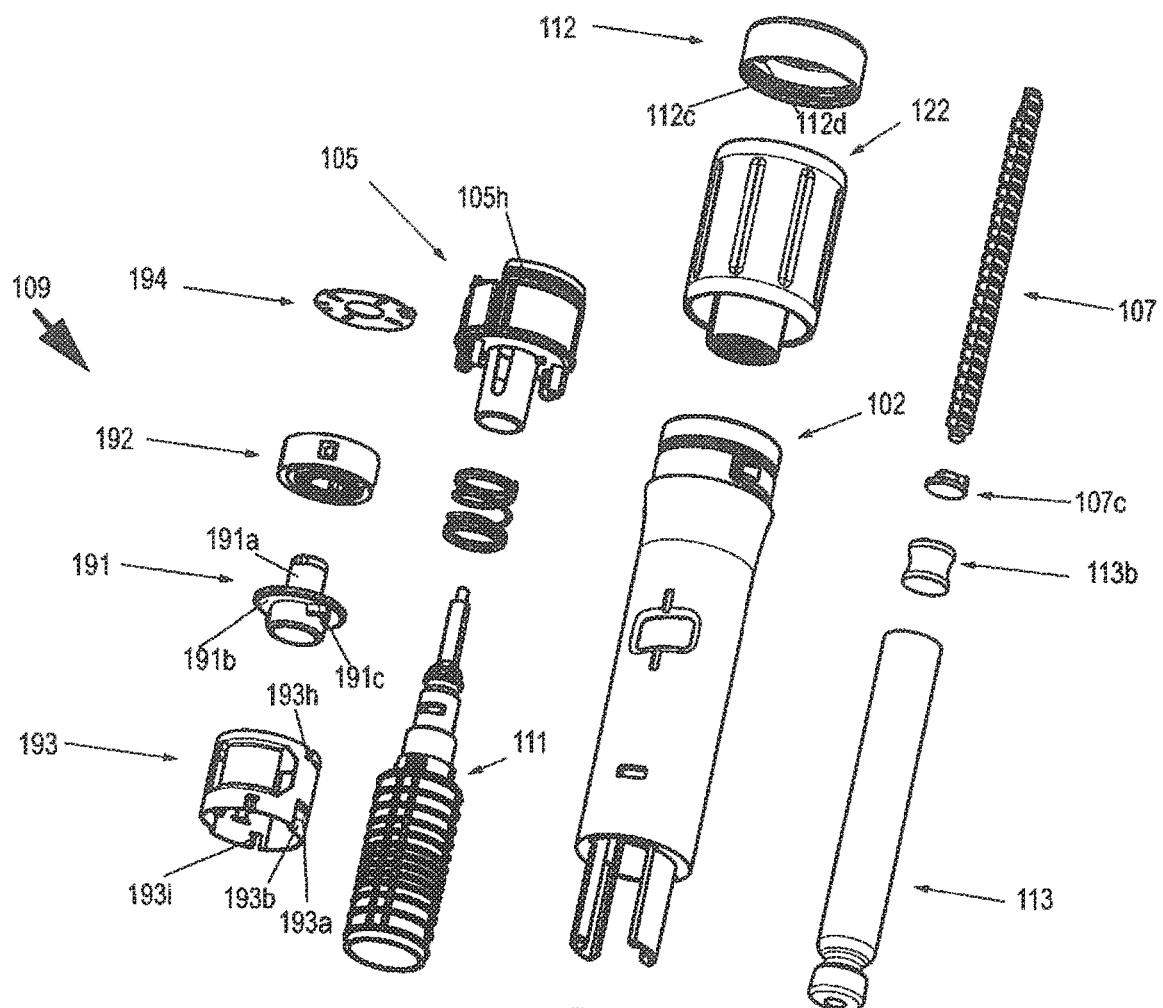
FIGS. 12a-12b are, respectively, exploded and cross-sectional representations of the injection device from FIG. 11.
Figure 12A:
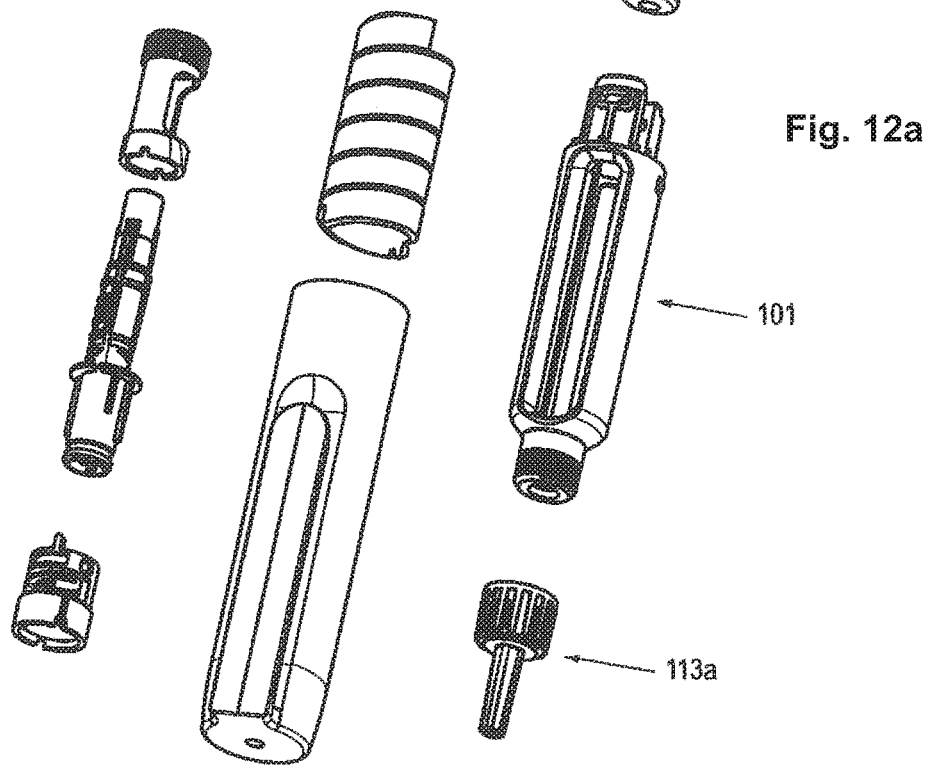

FIGS. 11-12d thereafter show the use of spring assemblies according to the invention in an alternative administration device, namely a so-called autopen, an injection pen by means of which a manually settable dose can be administered using stored energy.

Figure 1:
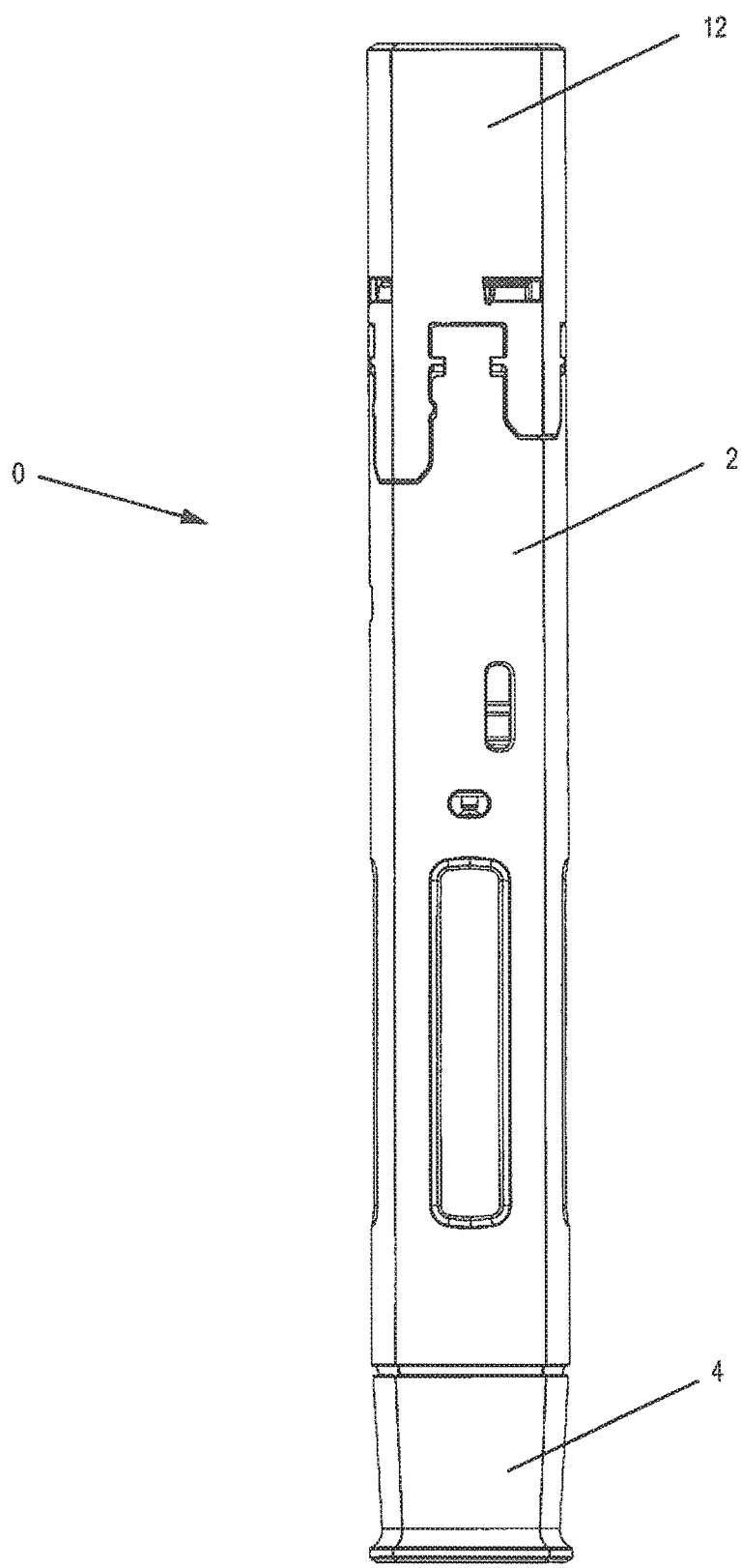
FIG. 1 is a view of an injection device according to the invention with a spring assembly according to the invention.

In reference to FIGS. 1-10d, below a first series of possible designs of the invention is described, based on an autoinjector 0 as represented in FIG. 1. Here, Swiss Patent Application 00904/15, which is a priority document to the instant application, is referenced and integrated in its entirety in the present application, since it also comprehensively describes the autoinjector 0 except for the spring assembly.

Figure 2A:
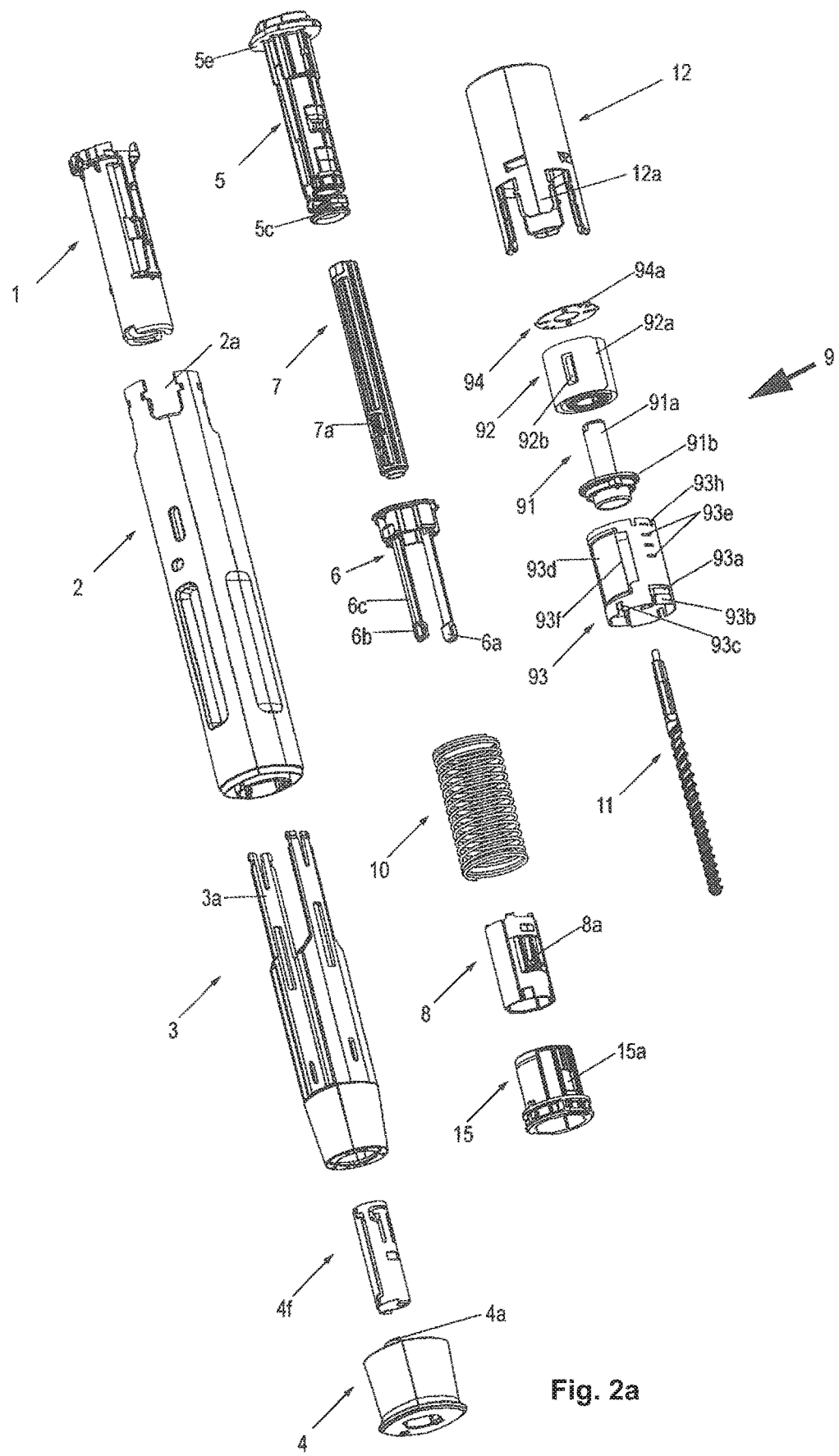
FIGS. 2a-2b are, respectively, an exploded view and a cross-sectional view of the injection device from FIG. 1.
Figure 2B:
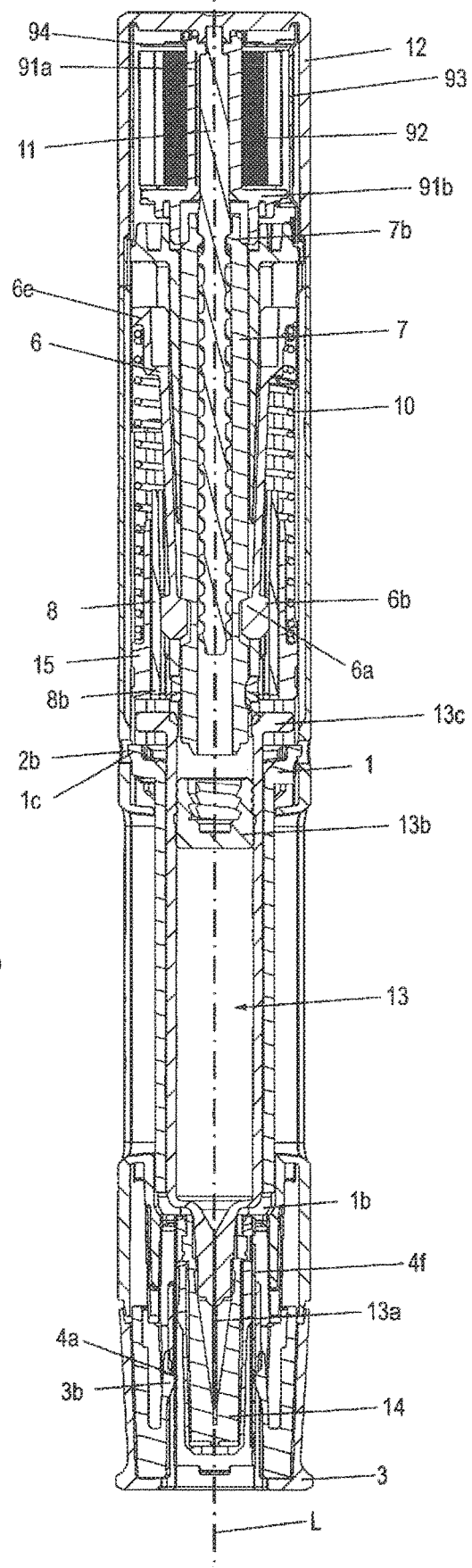

Next, the structure and function of the autoinjector 0 will be described in reference to FIGS. 1-2b. Autoinjector 0 has a sleeve-shaped elongate housing 2 with a longitudinal axis L which, at its proximal end, has a closure cap 12, which is connected by positive locking to the housing 2 in a rotationally and axially fixed manner and which forms the end of the autoinjector. The closure cap 12 is snapped onto the housing 2. For this purpose, the closure cap 12 has an engagement member 12a, which latches into a recess 2a on the housing 2, preferably in such a manner that the closure cap 12 is not detachable or not directly detachable from the housing 2.

On the distal end of the autoinjector, in its delivery state (FIGS. 2a-2b), a pull-off cap 4 with a cap remover 4f is arranged, which cap, before the use of the autoinjector, is pulled off, screwed off or turned off, and removed.

In the housing 2, a product container 13 in the form of a syringe is accommodated in an unshiftable manner relative to the housing 2—except for the assembly of the autoinjector—along the longitudinal axis L. The product container 13 comprises a sleeve-shaped syringe body, which encloses a piston 13b in a sealing contact with the inner periphery of the syringe body. On its distal end, the syringe body has an injection needle 13a, which, in particular, is non-detachably connected to the syringe body, and the distal end of which is formed by the needle tip. Between the injection needle 13a and the piston 13b, a liquid product, in particular a drug, is arranged within the syringe body, wherein the liquid product is dispensed by shifting the piston 13b in a dispensing direction, i.e., in the distal direction or toward the injection needle 13a through the hollow injection needle 13a from the product container 13. On its proximal end, the syringe body has a so-called finger flange, which protrudes radially outward over the outer circumference of the cylindrical syringe body.

The product container 13 is taken up in a product container holder, referred to as syringe holder 1, in such a manner that it is secured at least against a movement along the longitudinal axis L in the distal direction relative to the syringe holder 1. As can be seen best from FIG. 2b, the syringe holder 1 is connected by a positive locking to the housing 2, in particular latched. For this purpose, the housing 2 has recesses into which the latch elements, which are formed here on the proximal end of the syringe holder 1, engage. The syringe holder 1 has at least one inward protruding shoulder 1b, against which is braced a tapering section of the product container 13, which is attached distally of the cylindrical syringe body section guiding the piston 13b.

In order to prevent the product container 13 from being shiftable relative to the syringe holder 1 in the proximal direction, the product container 13 is pressed at its proximal end by a holder acting on the syringe body into engagement with the shoulder 1b. The holder is formed by a holding spring section 5c of a mechanism holder 5. The mechanism holder 5 is arranged, in particular, in a manner so it cannot be shifted along the longitudinal axis L relative to the housing 2 and/or in a rotationally fixed manner. The sleeve-shaped mechanism holder 5 can be snapped to the housing 2. By means of the holding spring section 5c, differences in the length of the product container 13, which can arise due to manufacturing tolerances, can be compensated, wherein the fixed seat of the product container 13 on the shoulder 1b is ensured.

The product container 13 is arranged relative to the housing 2 in such a manner that the needle tip protrudes distally over the distal end of the housing 2. In the start or delivery state of the autoinjector, i.e., when the pull-off cap 4 is arranged on the autoinjector, the needle 13a is covered by a needle protection cap 14 which, in the example shown, is formed as a so-called rigid needle shield known to the person skilled in the art, and alternatively as a soft needle shield, in order to protect the needle 13a against soiling or to keep the needle 13a and the drug sterile. The rigid needle shield 14 is arranged on a needle holding section of the syringe body, wherein the narrowing section of the syringe body is located between the needle holding section and the cylindrical section of the syringe body. The pull-off cap 4 is detachably snapped to the housing 2 or a needle protection sleeve 3, wherein this snap connection is released if the pull-off cap 4 is removed from the housing 2 or from the needle protection sleeve 3. In the example shown, the snap connection is formed by a snap hook 3b of the needle protection sleeve 3 and a snap geometry 4a of the pull-off cap 4. The pull-off cap 4 moreover comprises a cap remover 4f by means of which the rigid needle shield 14 is released from the product container 13 and removed together with the cover cap 4 from the autoinjector.

The autoinjector 0 has a needle protection sleeve 3, which is shiftable relative to the housing 2 and along the longitudinal axis L by an activation stroke $H_B$ (not shown) in the proximal direction into an actuated position, in order to trigger the product dispensation. In the start position of the needle protection sleeve 3, as shown in FIG. 2b, the distal end of the needle protection sleeve 3 protrudes distally over the needle tip of the needle 13a, so that access to the needle tip is at first prevented. By shifting the needle protection sleeve 3 by the actuation stroke $H_B$, the needle protection sleeve 3 is shifted in the proximal direction until the needle 13a protrudes from the distal end of the needle protection sleeve 3, protruding in particular with a length which corresponds to the injection depth of the needle into the puncture site. Preferably, the needle 13a should project sufficiently over the distal end of the needle protection sleeve 3 so that a subcutaneous or intramuscular injection can occur.

After the injection has occurred, the needle protection sleeve 3 can be shifted relative to the housing 2 from the actuated position along the longitudinal axis L by a needle protection stroke $H_N$ (not shown) in the distal direction into a needle protection position. In the needle protection position, the distal end of the needle protection sleeve 3 protrudes distally over the needle tip, so that access to the needle tip is prevented and the risk of injury is reduced. As described further below, the needle protection sleeve 3 can be blocked against renewed shifting back out of the needle protection position.

In particular, the autoinjector 0 moreover has a sleeve-shaped driving member 7, which, in particular on its inner side, has a threaded section, in particular a threaded segment 7b. The driving member 7 is, in particular, rotationally fixed with respect to the housing.

Moreover, as already mentioned, the autoinjector 0 comprises a rotation member 11, in particular a threaded rod 11, the rotation of which has the effect that the spring energy can be transferred to the driving member 7, as a result of which the driving member 7 is moved in the distal direction, in particular by a threaded drive. The threaded rod 11 is connected to a first spring in the form of the spring assembly 9, which stores and, as needed, delivers the energy necessary for dispensing product. The threaded rod 11 is coupled to an end of the first spring 9, wherein the other end of the first spring 9 is connected to the closure cap 12.

The threaded rod 11 is axially fixed with respect to the housing 2 and can be braced at least in a preferably distal direction in an axially fixed manner against the housing part 12 (closure cap).

By a release of the driving member 7, the first spring 9 is enabled to move the driving member 7 in the distal direction. The first spring 9 is a spiral shaped spring which, in the start or delivery state of the autoinjector, is pretensioned with sufficient energy so that it can dispense the product contained in the product container 13, in particular, completely by rotation of the threaded rod 11 and with shifting of the driving member 7 by a dispensing stroke $H_A$ (not shown) from the product container 13. In the delivery state of the device, there is a separation between the piston 13b and the distal end of the driving member 7, so that the driving member 7 abuts only during the performance of the dispensing stroke $H_A$ against the piston 13b and moves said piston along in the dispensing direction.

In an advantageous alternative design (not shown) of the threaded connection between threaded rod 11 and driving member 7, in particular, the thread of the threaded rod 11 can have a variable (thread) pitch, wherein, in a first area, the thread can have a high pitch, and, in other areas, different pitches are possible. For tolerance reasons, in the delivery state of the autoinjector 0, there can be a separation between driving member 7 and piston 13b. In production, an attempt is made to keep the separation as small as possible, so that the impact of the driving member 7 against the piston 13b does not lead to glass breakage. This separation between driving member 7 and piston 13b is also referred to as acceleration path. In order to be able to control or brake the acceleration of the driving member 7 in the acceleration path and to minimize the risk of glass breakage, for the start of the piston rod movement, a thread lead-in path having a high pitch in particular on the threaded rod 11 and/or driving member 7 is selected. Preferably, the axial section of the thread lead-in path must be greater than the acceleration path. Moreover, in a storage position, the axial forces, which are generated in particular by the thread transmission from the torque of the spring, can be kept small by a high pitch. The thread or the thread pitch can vary over the length of the threaded rod 11 and/or of the driving member 7. The thread can be single-start or multi-start. The thread is preferably two-start. The pitch can be progressive or degressive. For example, an additional area of the rotation member can have a smaller pitch than the first area, as a result of which the highest thread pitch can preferably not be self-locking. By means of such a varying pitch, it is possible to compensate for the decrease of the spring force torque and to keep the discharge force in a constant range during discharging. It is possible that, at the end of the discharging movement, a small thread pitch is selected, and thus the dispensing force is increased so that, for example, a stopper frictional force, which can increase at the end of the dispensing, is compensated, and a complete dispensing can be ensured. The rotation member and/or the driving member can have several areas with different thread pitches. For example, the thread can have a high thread pitch for the thread lead-in, and, subsequently, it can have an area with a continuously smaller thread pitch—for slow dispensing—and it can end in an area with a smaller thread pitch—in order to ensure complete dispensing. By means of a suitable construction of the thread connection, the selection of the spring 92 in the spring assembly 9 is thus simplified, because the drive train can compensate variations in the spring force deployment.

Furthermore, the autoinjector 0 has a holding element 6, which comprises two arms 6c in this example, wherein, on each arm 6c, a first engagement element 6a and a second engagement element 6b are arranged. The first engagement element 6a points radially towards the longitudinal axis L, wherein the second engagement element 6b points radially away from the longitudinal axis L. The first engagement element 6a engages in a recess 7a, which is formed by the driving member 7, whereby a movement of the driving member 7 relative to the holding element 6 in the distal direction or in the dispensing direction is prevented. As a result, the first spring 9 is held in its tensioned state.

The autoinjector 0 comprises a switching module 8, 15, which comprises a switching sleeve 15 and a locking sleeve 8 enclosed by the switching sleeve 15. In the delivery state of the device, the first engagement element 6a is held in engagement with the recess 7a by the inner circumference of the locking sleeve 8, which is in contact with the second engagement element 6b.

The switching sleeve 15 is connected to the proximal end 3a of the needle protection sleeve 3 or is in contact with at least the proximal end 3a of the needle protection sleeve 3. A second spring 10, which preferably at least partially encloses the switching sleeve 15 and the locking sleeve 8, is braced with its distal end against the switching sleeve 15. A part of the switching sleeve 15 is thus arranged between the needle protection sleeve 3 and the distal end of the second spring 10. The second spring 10 is a metal spring acting as a pressure spring and formed as a coil spring. The second spring 10 is braced with its proximal end against the holding element 6, in particular against a protrusion 6e, which engages in an axially shiftable manner and rotationally fixed manner in the housing 2. The second spring 10 thus also encloses the mechanism holder 5 at least partially, preferably completely.

The switching sleeve 15 has a recess 15a, into which a locking member 8a of the locking sleeve 8 engages. The locking member 8a is sawtooth-shaped and projects radially away from the longitudinal axis L. The locking member 8a is arranged resiliently on an arm, which is formed by the locking sleeve 8. By shifting the switching sleeve 15 in the proximal direction, the locking sleeve 8 is driven via the engagement of the locking member 8a in the proximal direction.

By shifting the needle protection sleeve 3 into the actuated position, the switching sleeve 15 is also driven by the actuation stroke $H_B$ (not shown), whereby the second spring 10 is tensioned. If the needle protection sleeve 3 is not shifted completely into the actuated position, the second spring 10 can shift the switching sleeve 15 and the needle protection sleeve 3 back again into the start position, wherein the locking sleeve 8 is also driven by the switching sleeve 15 via the engagement of the locking member 8a.

For administering the product from the product container 13, the pull-off cap 4 is removed from the autoinjector together with the rigid needle shield 14. The distal end of the needle protection sleeve 3 is set on the puncture site of a patient, wherein the housing 2 is shifted toward the puncture site, whereby the needle protection sleeve 3 is moved from its start position by the actuation stroke $H_B$ (not shown) in the proximal direction relative to the housing 2 into the actuated position. As a result, the second spring 10 is tensioned, wherein the switching sleeve 15 is driven by the needle protection sleeve 3 by the actuation stroke $H_B$. The locking sleeve 8 comprises a recess or a distal end 8b, which is moved by shifting the locking sleeve 8 by the actuation stroke $H_B$ along the longitudinal axis L to the position of the second engagement element 6b. As a result, the first engagement element 6a is moved from the engagement with the driving member 7 with a movement transverse to and away from the longitudinal axis L, wherein, at the same time, the second engagement element 6b is moved into engagement with the locking sleeve 8, in particular its recess 8b. As a result, the driving member 7 is released for the movement by the dispensing stroke $H_A$ (not shown) in the dispensing direction.

Since the axially fixed coupling between the driving member 7 and the holding element 6 is now released, the holding element 6, which can be moved at least a distance relative to the housing 2 and along the longitudinal axis L, can be moved by the second spring 10 in the proximal direction, wherein the holding element 6 drives the locking sleeve 8 by a start signal stroke $H_S$ (not shown) via the engagement of the second engagement element 6b into the recess 8b, whereby the locking sleeve 8 abuts against a start signal stop formed by the mechanism holder 5, and, as a result, issues an acoustic and/or tactile signal, which signals to the user of the device that the product dispensing has started.

Since the second engagement element 6b is still in the recess 8b of the locking sleeve 8, the holding element 6 is prevented as a result from moving further in the proximal direction relative to the housing 2 or the locking sleeve 8. The second engagement member 6b is held by the outer circumference of the driving member 7 in engagement with the recess 8b, when the driving member 7 is moved by its dispensing stroke $H_A$.

At the end of the dispensing stroke $H_A$, the driving member 7 releases the first engagement member 6a for a movement, in particular toward the longitudinal axis L, whereby the second engagement member 6b is moved out of engagement with the recess 8b of the locking sleeve 8, so that the second spring 10 accelerates the holding element 6 against the dispensing direction, i.e., in the proximal direction, so that, when the holding element 6 strikes the end signal stop 5e, an acoustic and/or tactile signal is generated.

By removing the autoinjector from the injection site, the second spring 10 can move the switching sleeve 15 and the needle protection sleeve 3 out of the actuated position into the needle protection position by the needle protection stroke $H_N$. A locking member 8a on the locking sleeve 8, which comes in engagement with the switching sleeve 15, then prevents a renewed shifting back of the needle protection sleeve 3.

Figure 3A:
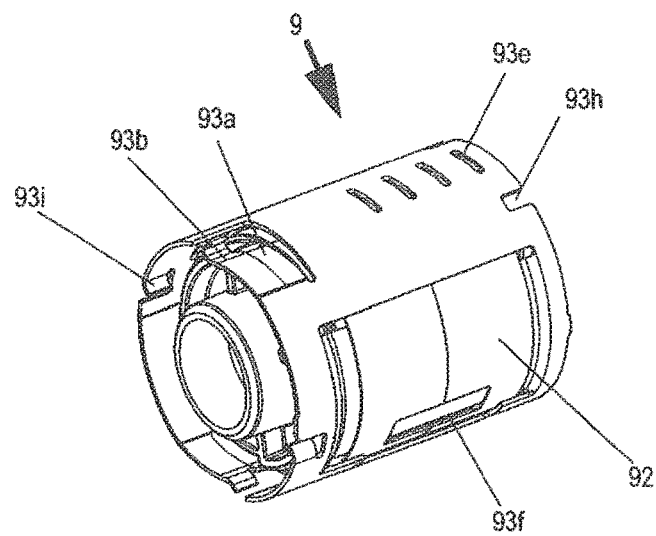
FIGS. 3a-3c are an isometric view, a cross-sectional view and an exploded view of a spring assembly according to the invention.
Figure 3B:
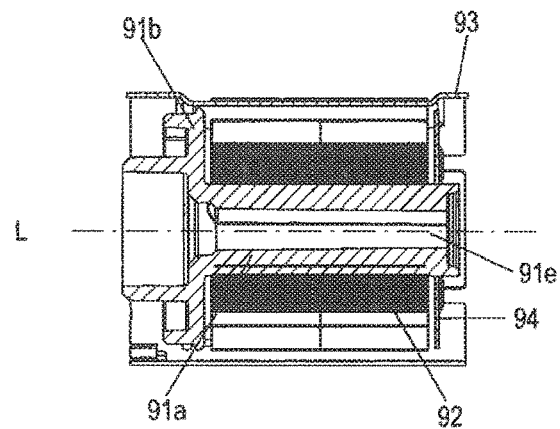
Figure 3C:
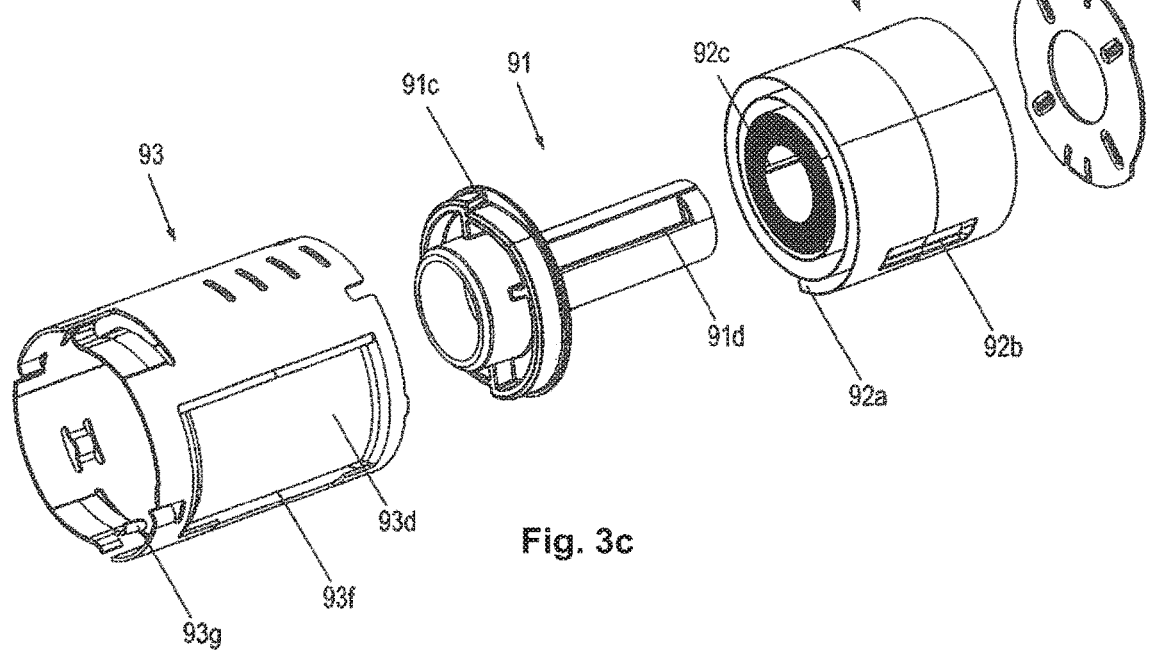
Figure 4A:
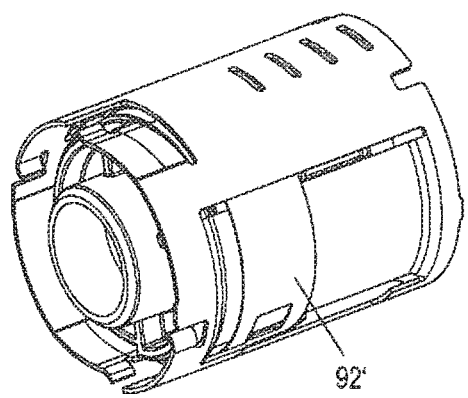
FIGS. 4a-4c are an isometric view, a cross-sectional view and an exploded view of a spring assembly according to the invention with an alternative design of the spiral spring.
Figure 4B:
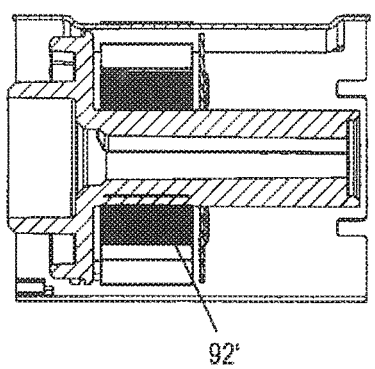
Figure 4C:
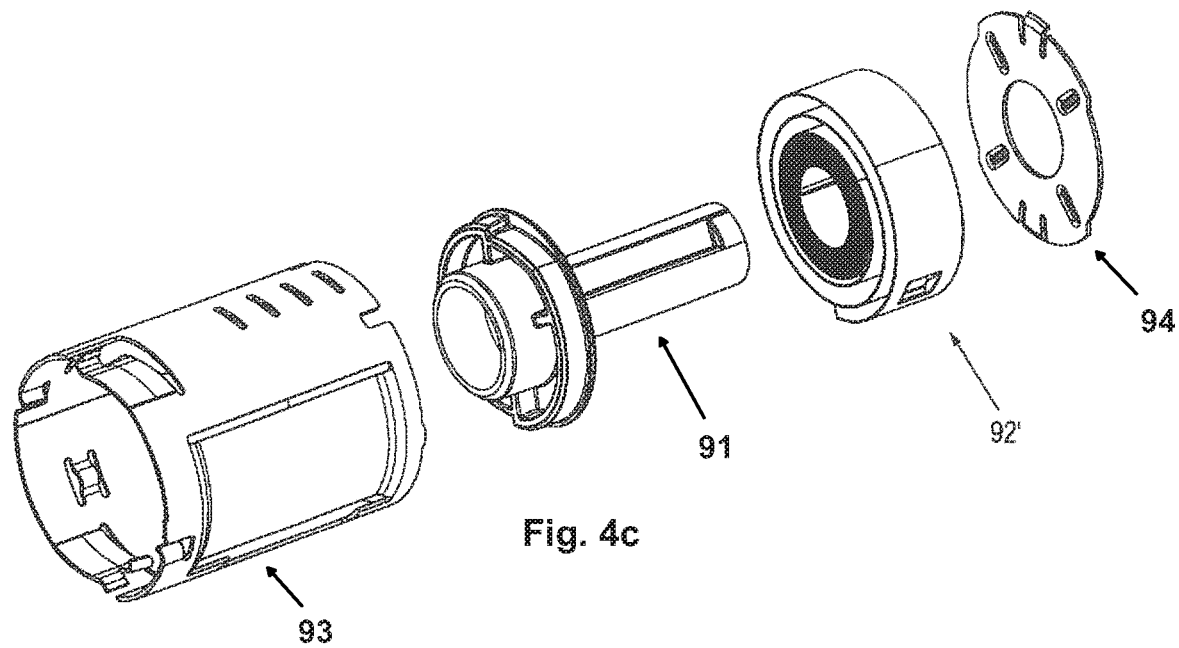

FIGS. 3a-3c show a first embodiment of a spring assembly according to the invention, which could be installed, for example, in autoinjector 0 or also in the autopen 100 described below. FIGS. 4a-4c show an embodiment with an alternative spiral spring.

FIG. 3a shows an isometric view of the spring assembly 9, FIG. 3b shows a longitudinal section through the spring assembly 9, and FIG. 3c shows an exploded representation of the spring assembly 9. The spring assembly 9 includes four separate parts, the spring shaft 91 with shaft 91a and flange 91b, the spiral spring 92, the spring sleeve 93 and the spring sleeve cover 94. The inner end of the spiral spring 92c is fastened by means of a holding flap in the spring anchoring 91d or holding rib, and in the process the spring 92 can be movably mounted in the axial direction L. The outer end of the spring 92a is fastened by means of flap 92b to the holding device 93d of the spring sleeve 93. Here too, a movement in the axial direction L between spring sleeve 93 and spring 92 can be possible. The flange 91b of the spring shaft 91 comprises one or more radial stops 91c, into which the locking snap device 93a of the spring sleeve 93 can engage by means of tooth 93g. The locking between the stop 91c/tooth 93g is selected here in such a manner that a relaxation of the spring 92 can be prevented. The spring shaft 91 has a bore or opening 91e in the axial direction L. In the opening, the proximal end of the threaded rod 11 can be mounted in a rotationally fixed manner. While the flange 91b closes off the spring assembly in the distal direction, the spring sleeve cover 94 is used for the closure in the proximal direction, wherein the spring sleeve cover 94 can be fastened by means of the fixation elements 94a protruding in the radial direction in the openings 93e of the spring sleeve 93. The spring assembly from FIGS. 4a-4c differs from the spring assembly from FIGS. 3a-3c with regard to the spring 92'. The band of the spiral spring 92' is smaller than that of the spiral spring 92. The comparison between the two variants shows one of the advantages of the design of the spring assembly 9 according to the invention. Without any resulting structural changes on spring shaft, spring sleeve or spring sleeve cover, springs of different size can be used. The administration apparatus, for example, the autoinjector 0 or the autopen 100, does not have to be structurally adjusted subsequently. Thus, without any change in the construction of the administration apparatus, an adaptation of the force that has to be exerted during the dispensing of a certain drug can occur merely by using a specifically adapted spring, wherein alternatively several springs can also be used, which result in the specific adaptation. The openings 93e made in different positions on the spring sleeve 93 make it possible that the spring sleeve cover 94 adapted to the band width of the spring 92 can be fastened in the spring sleeve 93, wherein, in the case of the alternate use of several springs, several covers can also be used.

In its distal area, the spring sleeve 93 comprises the locking snap device 93a as well as the control arm 93b. Both are parts of the same flexible arm, so that a movement of the free end of the control arm 93b in the radial direction results in a movement of the free end of the locking snap device 93a, in particular of the tooth 93g, in the same direction.

Figure 5A:
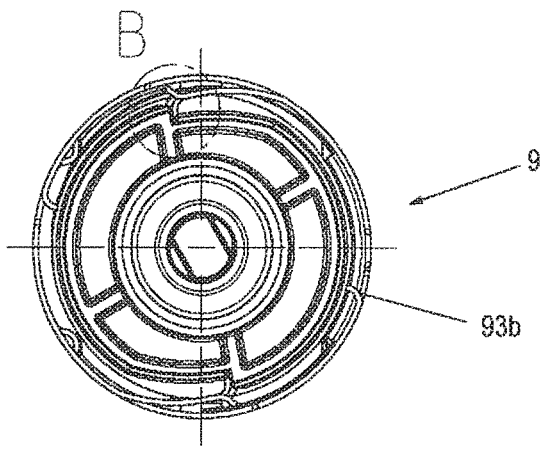
Figure 5B:
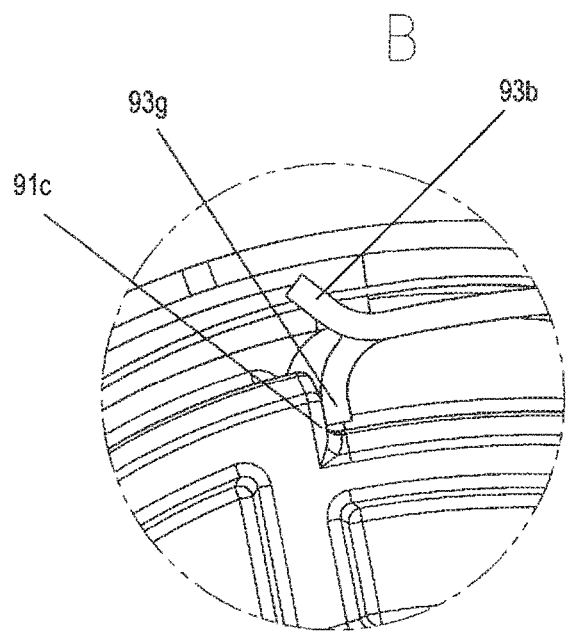

The spiral spring 92 can be tensioned by relative rotation of the spring sleeve 93 and the spring shaft 91. In the present example (FIGS. 3a-3c) and viewed in the proximal direction, the spring sleeve 93 is rotated counterclockwise relative to the spring shaft 91, in order to tension the spring 92 in the winding direction. If the spring 92 is tensioned, then the relaxation of the spring 92 via the engagement of locking snap device 93a in the radial stop 91c can be prevented. In a preferred variant, the spring sleeve 93 is formed from a metal plate, in which the locking snap device 93a can be brought in engagement with the radial stop via plastic deformation. Thus, potential energy can be stored in the spring assembly, and the assembly can also be transported or stored as bulk material when the spring is tensioned. FIGS. 5a and 5b show a view of the spring assembly 9 from the distal direction, wherein FIG. 5b is an enlarged detail from FIG. 5a. The engagement between tooth 93g and radial stop 91c can be seen very well particularly in FIG. 5b.

Figure 6:
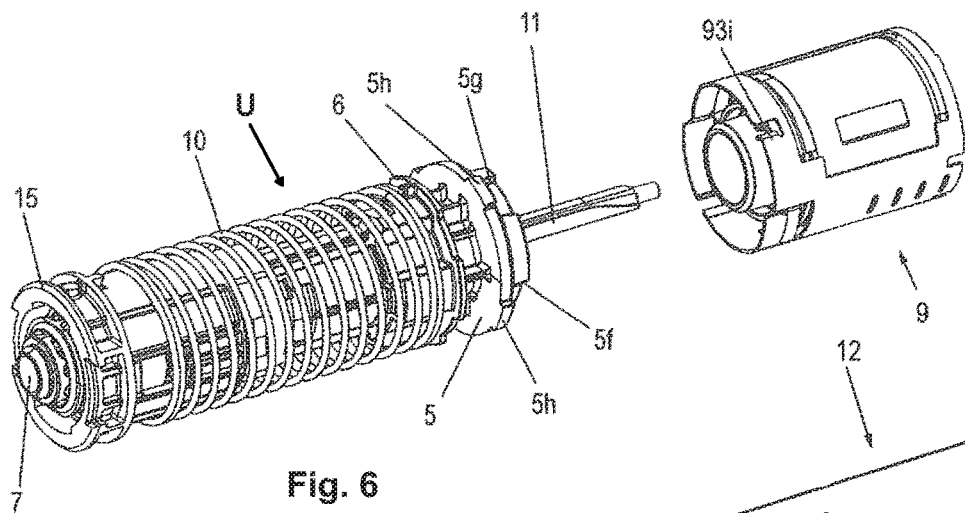
FIG. 6 is a view of the first assembly phase.
Figure 7A:
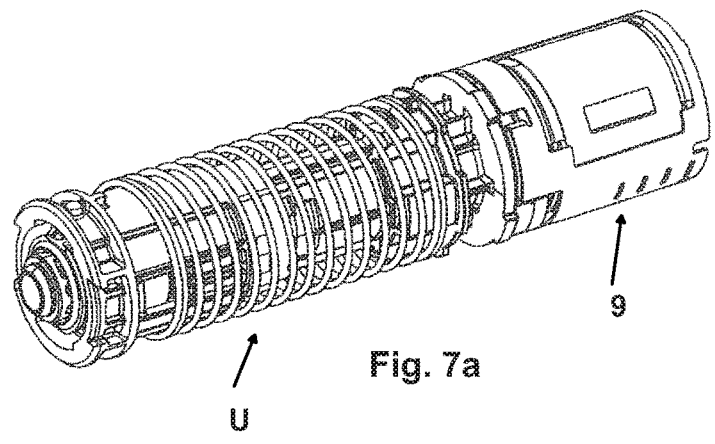
FIG. 7a is a view of the second assembly phase.
Figure 7B:
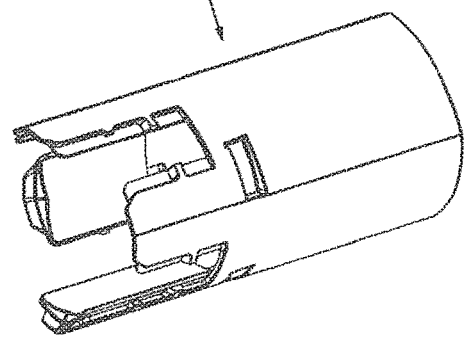
FIG. 7b is a view of the end cap with bayonet slot.
Figure 7B:
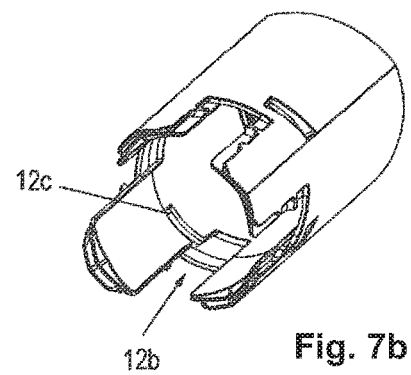
Figure 8:
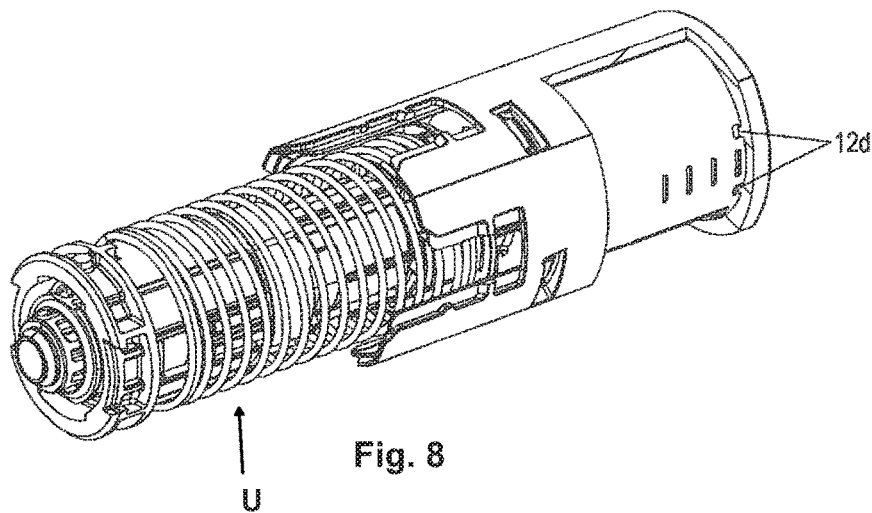
FIG. 8 is a view of the third assembly phase.

FIGS. 6 to 8 show the step-wise installation of the spring assembly 9 in the autoinjector 0. In a first step, the spring assembly is brought together with the preassembled drive unit U (left side, FIG. 6) of the autoinjector 0; it is important to mention here that, in particular, the driving member 7 is already assembled in a rotationally fixed manner in the mechanism holder 5 and that the holding element 6 is assembled in such a manner that the driving member 7 cannot be moved in the distal direction. Here, the spring assembly 9 is plugged onto the proximal end of the threaded rod 11. The cross-section of the proximal end of the threaded rod 11 is not circular here, and the opening 91e of the spring shaft 91 is designed to be complementary thereto, so that the two parts are rotationally fixed with respect to one another. During the plugging on, attention must be paid to the orientation of the mechanism holder 5, since the release element 5f should come to lie rotationally in front of the control arm 93b; see also thereto FIG. 9b, which is a cross-sectional representation of the situation with the spring assembly 9 plugged on. In FIG. 7a, the spring assembly 9 is brought together completely with the preassembled drive unit U.

Next, the closure cap 12 is connected over the spring assembly 9 with the preassembled drive unit U. Briefly summarized, the following occurs: the mechanism holder 5 and the closure cap 12 are firmly connected to one another via a bayonet closure. Moreover, the spring sleeve 93 is connected in a rotationally fixed manner to the closure cap 12, the locking engagement between locking snap device 93a and radial stop 91c is released, and, in a last step, a rotation of the spring sleeve 93 in the direction of a relaxation of the spring 92 due to engagement of the block 93i in the radial stop 5g of the mechanism holder 5 is prevented.

For the bayonet closure between mechanism holder 5 and closure cap 12, on the mechanism holder 5, bayonet lugs 5h are arranged (in the present case, there are four, wherein, in principle, at least one is used). On the inner surface of the closure cap 12, accordingly complementary bayonet slots 12b/c are arranged, wherein the grooves consist at least of an axially extending portion 12b as well as a part 12c extending along the periphery. The closure cap 12 is then shifted onto the preassembled drive unit in such a manner that the bayonet lugs 5h are inserted into the grooves 12b. In the process, the closure cap is shifted onto the drive unit sufficiently far so that the anti-rotation devices 93h of the spring sleeve 93 engage with the anti-rotation devices 12d of the closure cap 12, whereby closure cap 12 and spring sleeve 93 are connected in a rotationally fixed manner. Then, the closure cap 12 is turned relative to the mechanism holder 5, so that the bayonet lugs 5h now move further in the grooves 12c. Due to the anti-rotation device between closure cap 12 and spring sleeve 93, the spring sleeve 93 is also turned relative to the mechanism holder 5. The result of this is that the release elements 5f radially lift the associated control arms 93b, and as a result the associated connection between locking snap device 93a and radial stop 91c is also released. As an advantageous consequence, any pretensioning of the spiral spring 92 supports the closure movement of the bayonet closure until the block 93i of the spring sleeve 93 comes in abutment with the radial stop 5g of the mechanism holder 5, whereby the closure movement is completed. In this state, the torque of the spiral spring 92 is held on the outside via the radial stop 5g of the mechanism holder 5. On the inner side, the torque is transferred by the spring shaft 91 to the threaded rod 11. The threaded rod 11 itself—as described—is connected via a threaded connection to the driving member 7, which in turn is connected in a rotationally fixed manner to the mechanism holder 5, so that the torque is converted into a force which acts axially in the distal direction on the driving member. As shown in FIG. 2b, the driving member 7 is prevented by the engagement of the engagement element 6a in the recess 7a before the release of the autoinjector 0 from moving in the distal direction. The spiral spring 92 is thus also stably assembled in this phase of the assembly of the autoinjector 0, so that any pretensioning present would be lost. The final assembly of the autoinjector 0 can thus be continued in a manner familiar to the person skilled in the art.

Figure 9A:
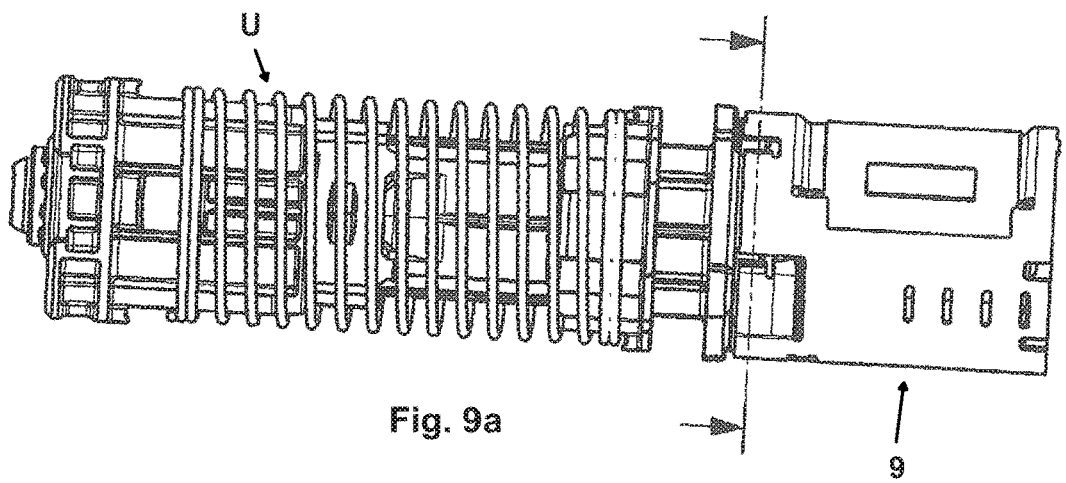
FIGS. 9a-d are views of a spring assembly according to the invention from a distal position in three different states during the assembly, wherein the mechanism holder is represented in partial cross-section.
Figure 9B:
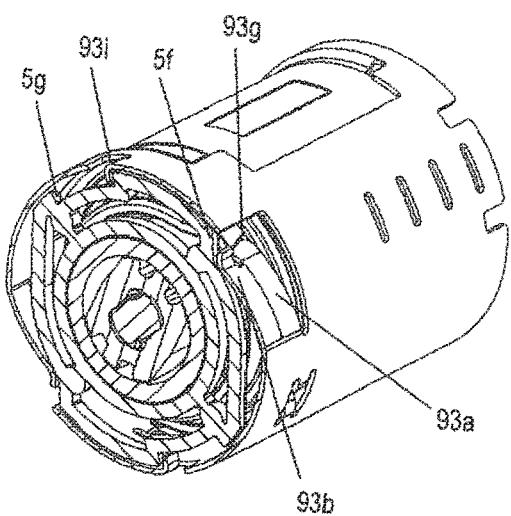
Figure 9C:
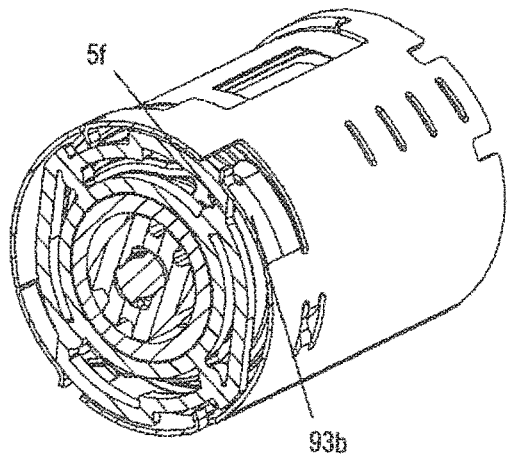
Figure 9D:
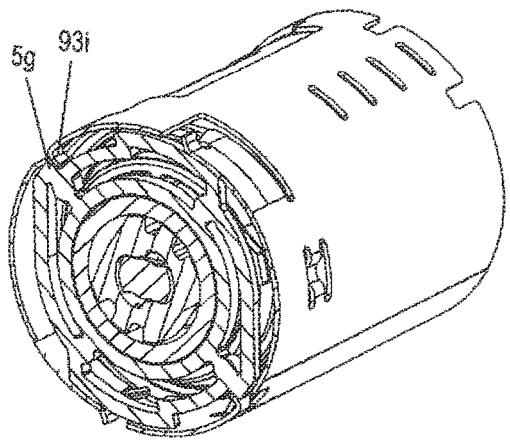
Figure 10A:
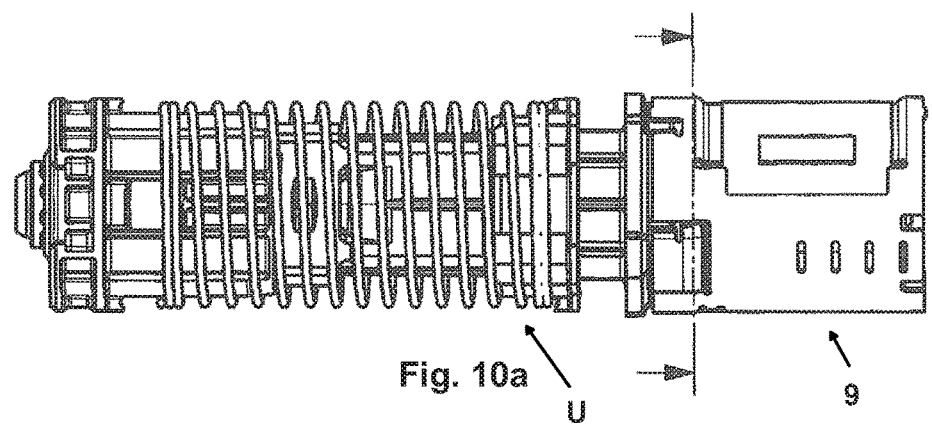
FIGS. 10a-d are views of the spring assembly from FIGS. 9a-d, wherein a distal part of the spring assembly is shown in partial cross-section to better show the locking snap device.
Figure 10B:
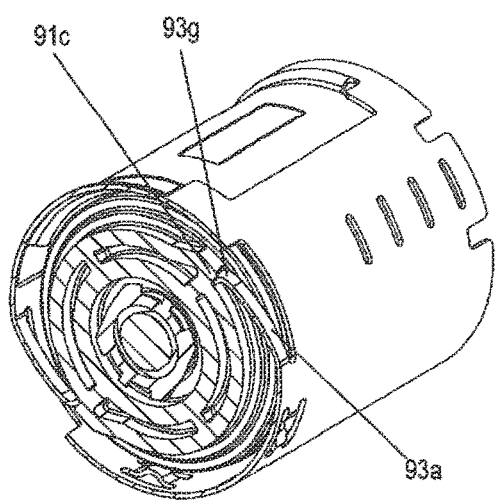
Figure 10C:
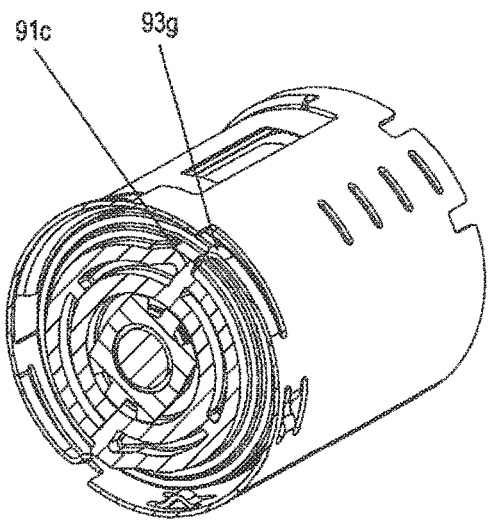
Figure 10D:
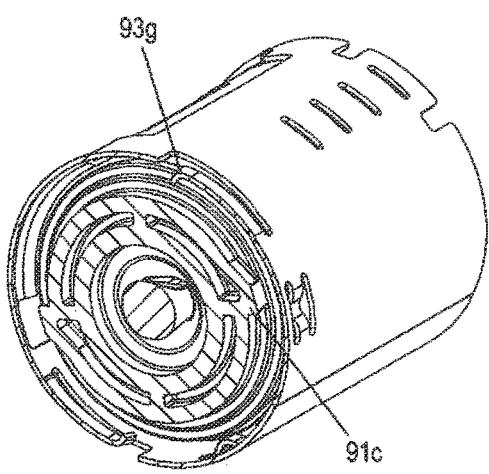

The above-described phases of the assembly of preassembled drive unit, spring assembly and closure cap are documented additionally also in FIGS. 9a-9d and 10a-10d. In FIGS. 9b-9d, it is shown how the release element 5f lifts the control arm 93b, whereby the connection between locking snap device 93a and radial stop 91c is released, and subsequently the radial block 93i of the spring sleeve 93 engages with the radial stop 5g of the mechanism holder 5. FIGS. 10b-10d show the same phases as FIGS. 9b-9d, wherein the cross-section is at the level of the locking snap device 93a.

Figure 12B:
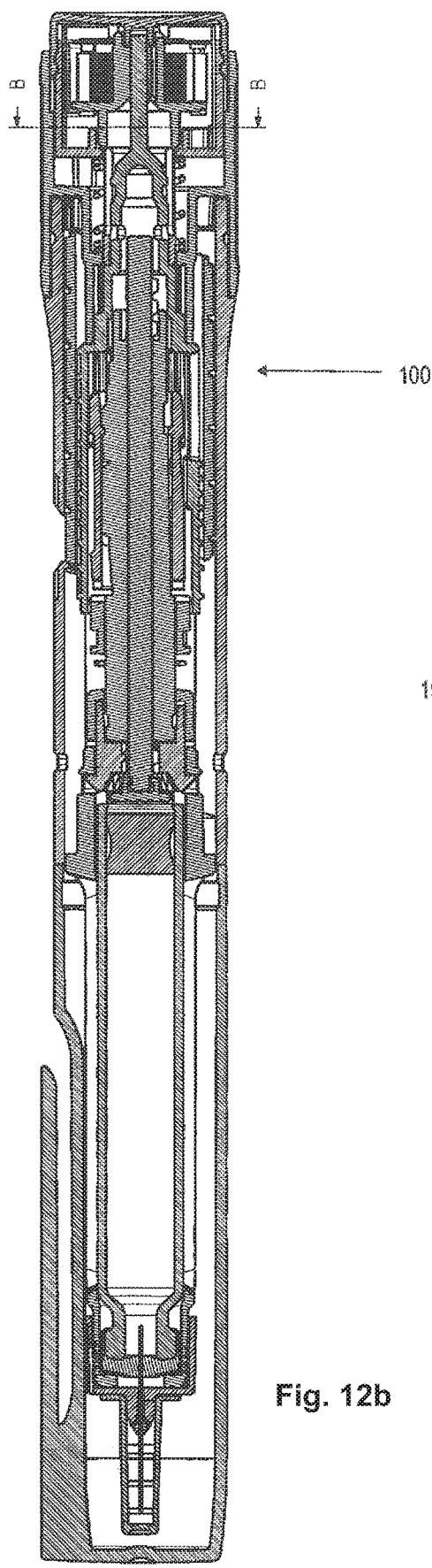

In reference to FIGS. 11 to 12b, a second possible administration device according to the invention, with spring assembly according to the invention, is described below, based on an automated injection pen 100, as represented in FIG. 11; the administration device 100 is referred to below simply as autopen. Here, reference is made to WO2015/135083, which is incorporated by reference in its entirety in the present application, since it also conceptually describes the autopen 100 except for the spring assembly.

The spring assembly 109 is structured analogously to spring assembly 9; accordingly, corresponding parts and features are marked with a reference numeral plus 100. As an example, the spiral spring 192 of the autopen 100 is mentioned, which in autoinjector 0 corresponds to the spiral spring 92. The same applies to analogous parts in the administration device.

Figure 12C:
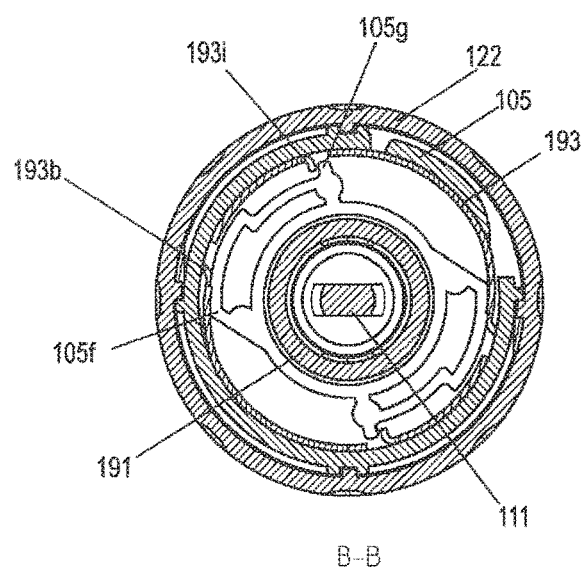
FIG. 12c is a detailed cross-section of FIG. 12b along line B-B.

The autopen 100 is designed in such a manner that several injections with variable dose can be administered by the user. If the drug container 113 is empty, the autopen 100 is disposed of as a whole. The spiral spring 192 of the spring assembly 109 is here designed in such a manner that it is pretensioned, and the entire drug container 113 can be emptied with the stored energy. In autopen 100, the spring assembly 109 is located in the dose setting member 122. Here, the spring shaft 191 is connected in a rotationally fixed manner to the driving member 111. In the assembled state, as shown in FIGS. 12b and 12c, the engagement of the radial block 193i of the spring sleeve 193 into the radial stop 105g of the spring recess 105 prevents a relaxation of the spiral spring 192.

The assembly of the spring assembly 109 and the release of the torque from the spiral spring 192 occur correspondingly almost in the same way as in the autoinjector 0. During the assembly, the spring recess 105 performs the functions of the mechanism holder 5; the driving member 111 corresponds to the threaded rod 11, and cover 112 corresponds to the closure cap (or housing part) 12. At least dosing element 122, spring recess 105 and driving member 111 are preassembled in such a manner that all three parts are arranged in a rotationally fixed manner with respect to one another.

The geometry of the cover 112 results in a difference in the assembly. Instead of being connected by a bayonet closure, the cover 112 is connected via a snap connection to the spring recess 105. For this purpose, on the periphery of the spring recess 105, a groove 105h is arranged, and complementary thereto, a rib 112c is arranged on the inner surface of the cover 112. Functionally, the rib 112c corresponds to the bayonet slot 12c of the autoinjector 0. During the assembly, first the spring assembly is shifted into the spring recess 105, and the spring shaft 191 is connected in a rotationally fixed manner to the driving member 111. Then, the cover 112 is snapped onto the spring recess 105 (which functionally corresponds to the first part of the bayonet closure process in the autoinjector 0), wherein the anti-rotation device elements 112d of the cover 112 have to be oriented in such a manner that they can engage in the anti-rotation elements 193h of the spring sleeve 193. After the cover 112 has properly snapped on, the cover 112 can be turned relative to the spring recess 105, wherein the release elements 105f move the associated control arm 193b radially outward and thus release the engagement of locking snap device 193a and radial stop 191c on the spring shaft 191. The torque acting on the spiral spring 192 now has the effect that the cover 112 together with the spring sleeve 193 is rotated relative to the spring recess 105 until the block 193i of the spring sleeve 193 engages with the radial stop 105 of the spring recess.

For the autopen 100, simple assembling variants can also advantageously be designed. Thus, for example, the engagement between locking snap device 193a and the radial stop 191c can also be released without the cover 112 in a variant. This can occur in such a manner that, after the spring assembly 109 has been shifted into the spring recess 105, the spring sleeve 193 is turned directly relative to the spring recess, and the release elements 105f, as described above; then actuate the control arm 193b. The cover 112 could thus be subsequently snapped onto the spring recess 105. An anti-rotation device 112d/193h would then be obsolete.

Furthermore, in another advantageous simplification, it would also be conceivable for the control arm 193b to be actuated already during the shifting of the spring assembly 109 into the spring recess 105, and thus no relative rotation between spring sleeve 193 and spring recess 105 would be necessary for the release of the torque.

What is claimed is:

1. A spring assembly for an administration device, comprising
   a driving spring;
   a spring shaft defining a spring axis and comprising a flange fixedly attached to the spring shaft proximate a distal end of the spring shaft and extending radially away from the spring axis, wherein an inner end of the spring is coupled to the spring shaft in a rotationally fixed manner;
   a spring sleeve, which at least partially surrounds an outer circumferential region of the spring, wherein an outer end of the spring is connected to the spring sleeve in a rotationally fixed manner;
   at least one blocking element and complementary radial stop arranged on the spring sleeve and the flange, such that the spring sleeve and the spring shaft can be releasably rotationally secured in relation to each other to prevent spring relaxation when the blocking element and the radial stop engage; and
   at least one control element adapted to release an engagement of the blocking element and the radial stop when being moved by a release element of a drive unit of the administration device upon connecting the spring shaft of the spring assembly to a rotatable driving member of the drive unit.

2. The spring assembly of claim 1, further comprising a radial block adapted to engage a radial stop of the drive unit to produce a force-transmitting connection between the spring assembly and the drive unit from a rotation between the spring sleeve and the drive unit triggered by the release of the engagement of the blocking element and the radial stop of the spring assembly.

3. The spring assembly of claim 1, wherein the at least one control element includes a control arm which is moved radially outward by the release element and thus releases a force present in the spring assembly.

4. The spring assembly of claim 3, wherein the control arm is arranged at the free end of the flexible arm axially offset in a distal direction from the blocking element, and wherein upon radial deflection of the control arm, the blocking element is radially moved correspondingly.

5. The spring assembly of claim 1, wherein the spring sleeve is arranged coaxially to the spring shaft, the spring sleeve comprising at least one flexible arm extending in a circumferential direction of the spring sleeve, wherein one end of the flexible arm is attached to the spring sleeve and a free end of the flexible arm is configured to be deflected in a radial direction, wherein, at the free end, the blocking element is arranged and configured as a tooth, which, due to deflection of the at least one flexible arm, can be made to engage with the radial stop or released from an engagement, such that the flexible arm together with the blocking element can form a locking snap device.

6. The spring assembly of claim 1, further comprising a disk-type spring sleeve cover extending radially away from the spring axis, which can be axially fixedly attached to the spring sleeve or to the spring shaft, wherein a disk diameter of the spring sleeve cover is less than or equal to a diameter of the spring sleeve.

7. The spring assembly of claim 1 wherein an axial positioning of the spring is defined by a fixed position of the flange and by a variable axial fixation of the spring sleeve cover such that springs having different axial extension may be accommodated in the spring assembly.

8. The spring assembly of claim 1, wherein the spring comprises a spirally wound band material.

9. The spring assembly of claim 1, wherein the spring shaft comprises an axially formed holding rib, in which the inner end of the spring can be anchored in a rotationally fixed manner, and wherein the spring sleeve comprises an axially oriented holding structure, on which the outer end of the spring can be anchored in a rotationally fixed manner.

10. The spring assembly of claim 9, wherein one or both of the inner end and the outer end of the spring is configured as a holding flap, to facilitate anchoring the spring in a rotationally fixed manner.

11. The spring assembly of claim 1, wherein the spring can be pretensioned prior to connecting the spring shaft of the spring assembly to the rotatable driving member of the drive unit, by a relative rotation of the spring sleeve toward the spring shaft, and wherein this pretensioning can be held by an engagement of the radial stop and the blocking element of the spring assembly.

12. The spring assembly of claim 11, wherein the pretensioning corresponds to a torque of 1 to 100 N/mm, or from 30 to 80 N/mm, or from 60 to 70 N/mm.

13. An administration device for administering a liquid product, the administration device comprising a spring assembly according to claim 1 and a drive unit, wherein a rotatable driving member of the drive unit is connected to the spring shaft of the spring assembly in a rotationally fixed manner.

14. The administration device of claim 13, wherein the rotatable driving member is a threaded rod.

15. The administration device of claim 13, further comprising:
a housing with a mechanism holder which is firmly connected to the housing;
an injection release actuator;
a product container, comprising an axially shiftable stopper for dispensing product,
wherein the product container is arranged at least axially fixedly to a portion of the housing;
wherein the spring assembly stores energy for automatic dispensing of product and the spring assembly is operatively connected to the release device, and
wherein the spring sleeve is connected to the housing in a rotationally fixed manner; and a piston rod arranged coaxially relative to the longitudinal axis, which is guided axially shiftably and in a rotationally fixed manner in the mechanism holder, wherein the piston rod is axially movable to shift the stopper in the distal direction and the piston rod is sleeve-like and in a threaded engagement with the rotatable driving member via threaded elements on an inner surface of the piston rod, such that rotation of the rotatable driving member causes an axial shifting of the piston rod.

16. The administration device of claim 15, configured for automatic administration as a patch device, an injection pen, or an autoinjector for accommodating a pre-filled syringe with an injection needle non-releasably connected to the product container.

17. A method for assembling a spring assembly with a pretensioned driving spring according to claim 1 in an administration device for administering a liquid product, comprising; shifting axially the spring assembly onto a preassembled drive unit of the administration device; connecting a rotatable driving member of the drive unit, in particular a threaded rod, to a spring shaft of the spring assembly in a rotationally fixed manner; and
moving, by a release element of the drive unit, the at least one control element of the spring assembly, to release an engagement of the blocking element and the radial stop of the spring assembly.

18. The method of claim 17, wherein the administration device comprises a housing and a mechanism holder rigidly connected to the housing, comprising at least the following steps:
a) shifting a housing part or closure part of the administration device in a distal direction axially over the spring assembly, whereby an outer circumferential surface of the spring assembly is connected in a rotationally fixed manner to the housing part or closure part,
b) axially shifting the spring assembly onto a preassembled drive unit of the administration device which comprises the mechanism holder, whereby a release element arranged on the mechanism holder is shifted in front of a control arm of the spring assembly;
c) rotating the housing part or closure part relative to the spring assembly and preassembled drive unit;
whereby guide elements of the mechanism holder are guided in a guide of the housing part or closure part, wherein the guide extends along a periphery of the housing part or closure part, and
wherein due to the turning, the release element moves the control arm in a radial direction outward and releases a torque present in the spring assembly, whereby an additional relative rotation between housing part or closure part and the mechanism holder is triggered until a radial block of the spring assembly engages with a radial stop of the mechanism holder to thereby provide a force-transmitting connection between the spring assembly and the mechanism holder.

19. The spring assembly of claim 1, wherein the at least one blocking element is on the flange and the complementary radial stop is on the spring sleeve.

* * * * *